(12) United States Patent
Kassab et al.

(10) Patent No.: US 9,555,228 B2
(45) Date of Patent: *Jan. 31, 2017

(54) SYSTEMS, DEVICES, AND METHODS FOR LOCALIZED DRUG DELIVERY

(71) Applicant: DTherapeutics, LLC, Zionsville, IN (US)

(72) Inventors: Ghassan S. Kassab, La Jolla, CA (US); Jose A. Navia, Sr., Buenos Aires (AR)

(*) Notice: Subject to any disclaimer, the term of this patent is extended or adjusted under 35 U.S.C. 154(b) by 301 days.

This patent is subject to a terminal disclaimer.

(21) Appl. No.: 14/028,838

(22) Filed: Sep. 17, 2013

(65) Prior Publication Data

US 2015/0080855 A1 Mar. 19, 2015
US 2016/0184567 A9 Jun. 30, 2016

Related U.S. Application Data

(63) Continuation of application No. 12/579,125, filed on Oct. 14, 2009, now Pat. No. 8,535,260.

(51) Int. Cl.
*A61M 37/00* (2006.01)
*A61K 9/00* (2006.01)
(Continued)

(52) U.S. Cl.
CPC ............ *A61M 37/00* (2013.01); *A61K 9/0024* (2013.01); *A61L 31/148* (2013.01); *A61L 31/16* (2013.01); *A61M 25/01* (2013.01); *A61M 31/002* (2013.01); *A61L 2430/20* (2013.01); *A61M 25/0082* (2013.01)

(58) Field of Classification Search
CPC ..... A61M 37/00; A61M 31/00; A61K 9/0024; A61L 31/16; A61L 31/148; A61B 17/0401; A61B 17/00004; A61B 2017/06176; A61B 2017/0456; A61B 2017/0412; A61F 2210/0004; A61F 2220/0016

See application file for complete search history.

(56) References Cited

U.S. PATENT DOCUMENTS 5,244,460 A 9/1993 Unger et al.
6,074,673 A 6/2000 Guillen
(Continued)

FOREIGN PATENT DOCUMENTS

WO WO 2006/058289 6/2006

OTHER PUBLICATIONS

International Searching Authority, International Search Report, mailed May 19, 2008 (PCT/US05/42911).

(Continued)

*Primary Examiner* — Bradley Osinski
(74) *Attorney, Agent, or Firm* — Reichel Stohry LLP; Mark C. Reichel; Natalie J. Dean

(57) ABSTRACT

Devices, systems, and methods for localized drug delivery. In at least one embodiment of a method of localized drug delivery, the method comprises the steps of placing a resorbable device within a tube, introducing the tube within a mammalian body at or near a tissue and/or organ within the mammalian body, and anchoring the resorbable device to the tissue and/or organ. Devices and systems useful for performing such a method are also disclosed herein, wherein an exemplary device comprises at least one drug release portion having at least one drug to be released over time and a binder intermixed with the at least one drug, and at least one resorbable anchor portion coupled to the at least one drug release portion.

20 Claims, 13 Drawing Sheets

(51) Int. Cl.
*A61L 31/16* (2006.01)
*A61L 31/14* (2006.01)
*A61M 31/00* (2006.01)
*A61M 25/01* (2006.01)
*A61M 25/00* (2006.01)

(56) References Cited

U.S. PATENT DOCUMENTS

| | | |
|---|---|---|
| 6,309,367 B1 | 10/2001 | Boock |
| 6,371,904 B1 | 4/2002 | Sirimanne et al. |
| 6,632,196 B1 | 10/2003 | Houser |
| 6,962,574 B1 | 11/2005 | Noblitt et al. |
| 7,303,571 B2 | 12/2007 | Makower et al. |
| 8,361,101 B2 | 1/2013 | Kassab |
| 8,894,681 B2 | 11/2014 | Kassab |
| 2002/0082636 A1 | 6/2002 | Sawhney et al. |
| 2004/0098030 A1 | 5/2004 | Makower et al. |
| 2004/0098118 A1 | 5/2004 | Granada et al. |
| 2008/0195138 A1 | 8/2008 | Kassab |
| 2013/0144324 A1 | 6/2013 | Kassab |

OTHER PUBLICATIONS

International Searching Authority, Written Opinion of the International Searching Authority, mailed May 19, 2008 (PCT/US05/42911).

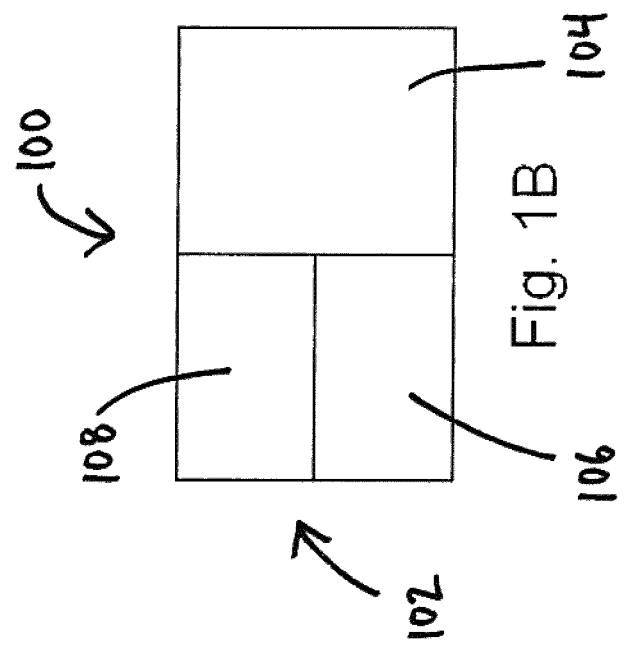
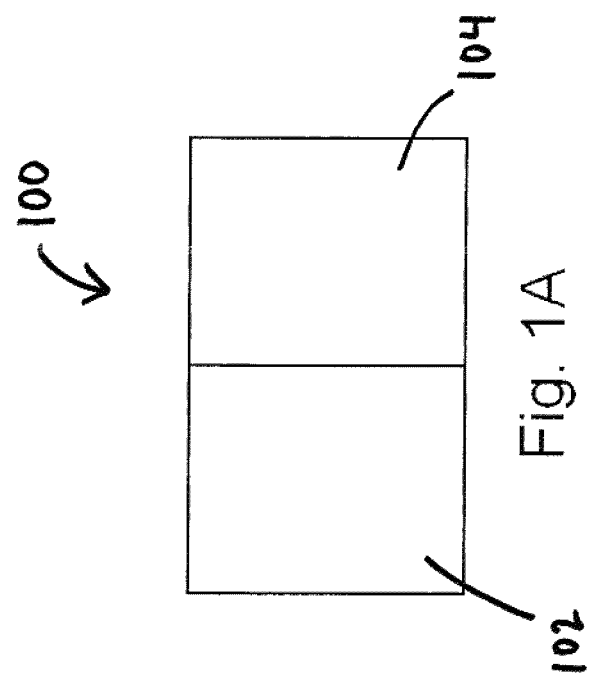

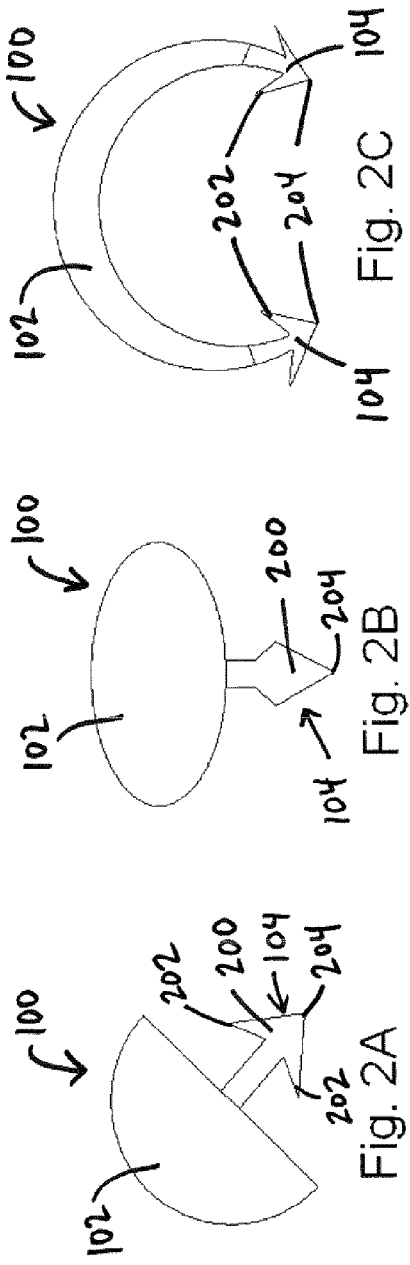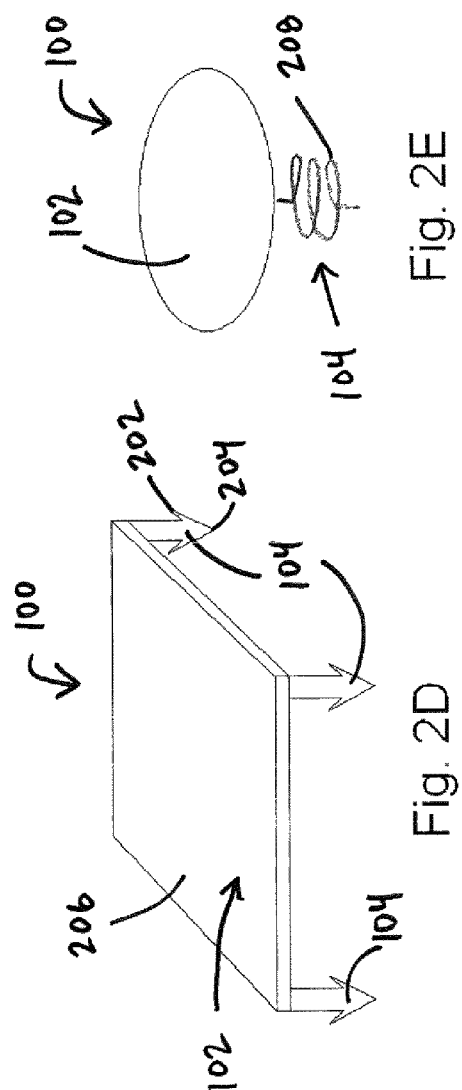

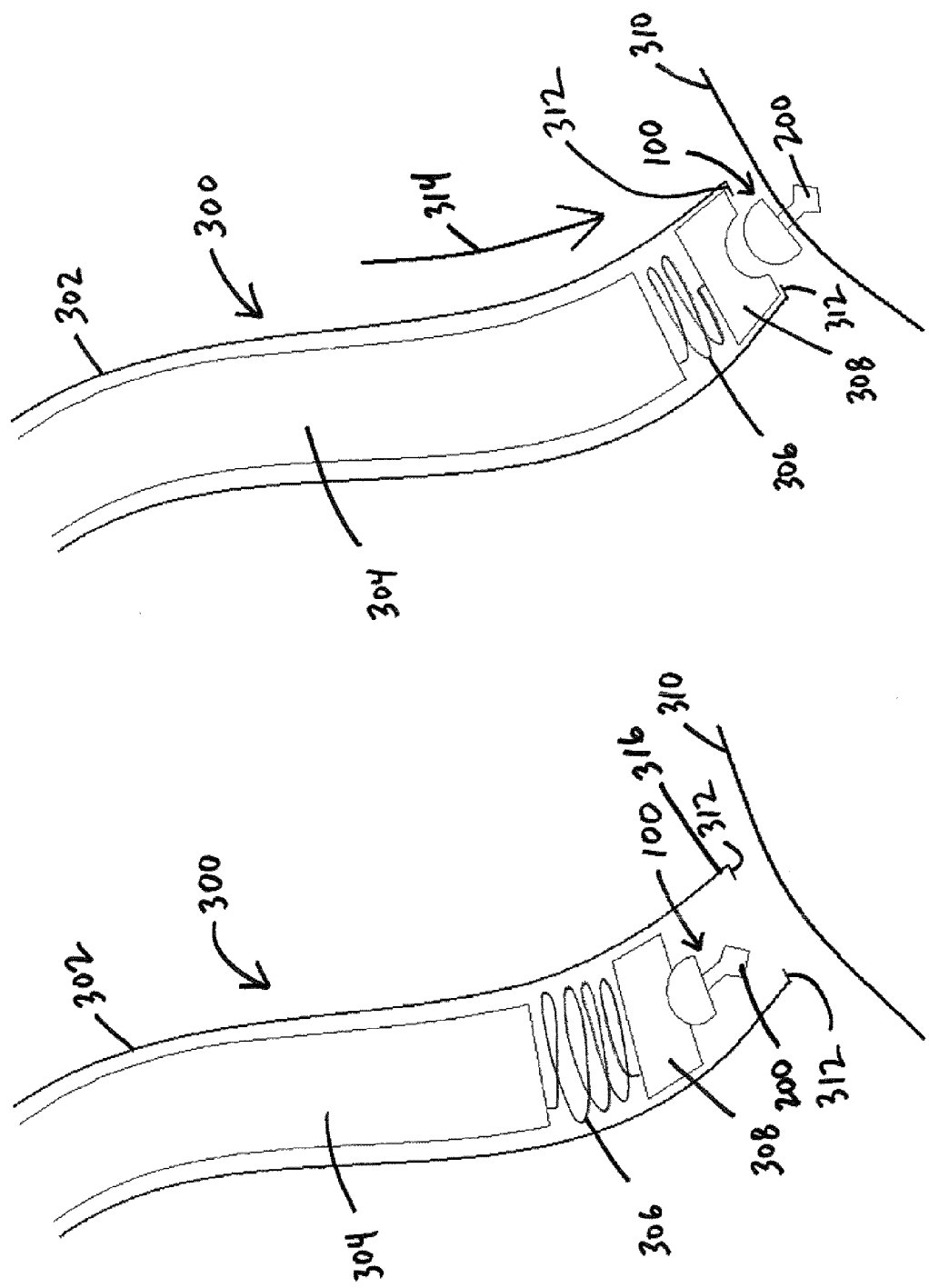

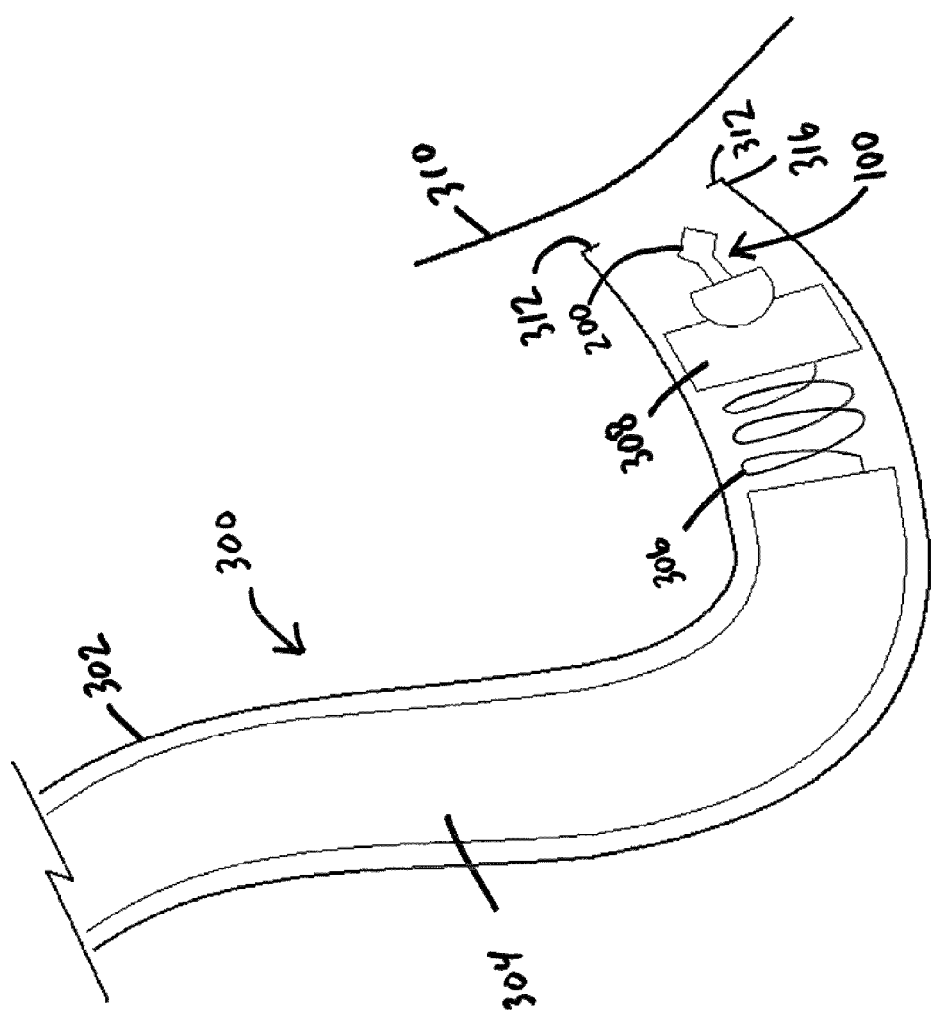

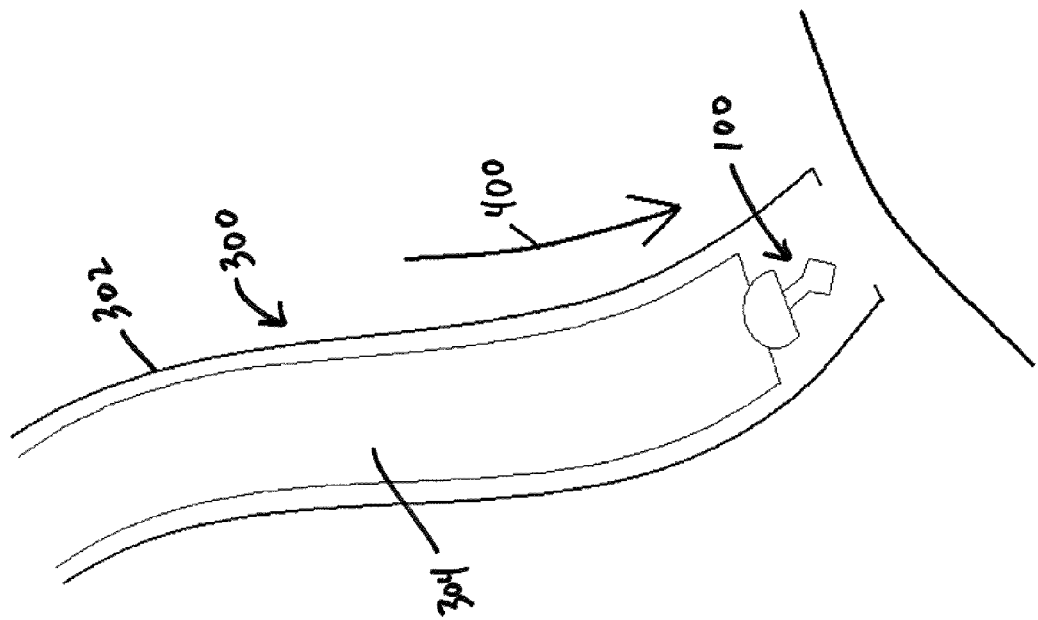
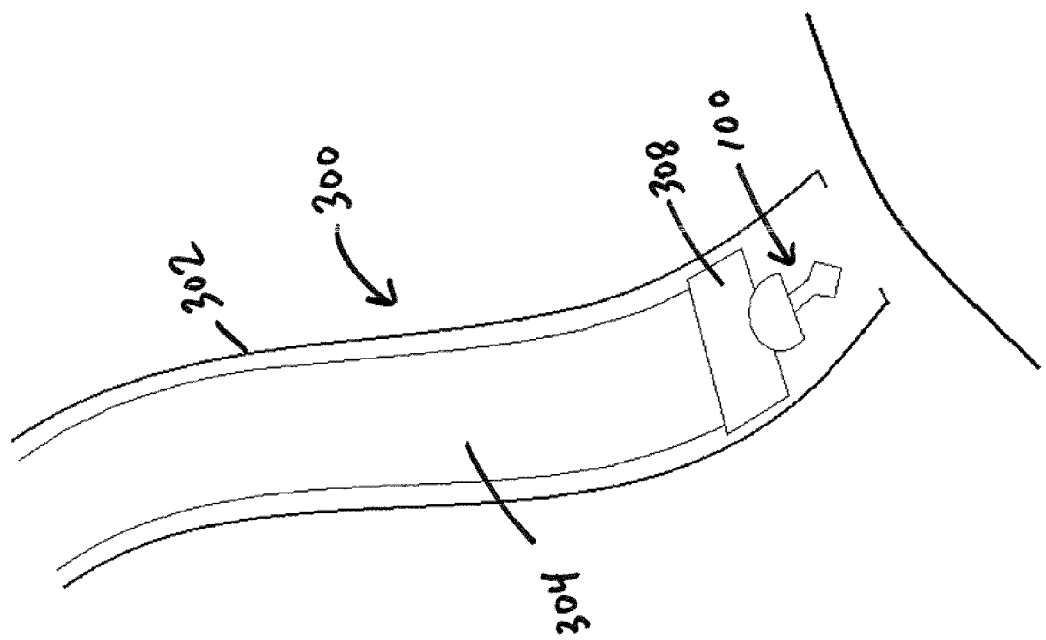

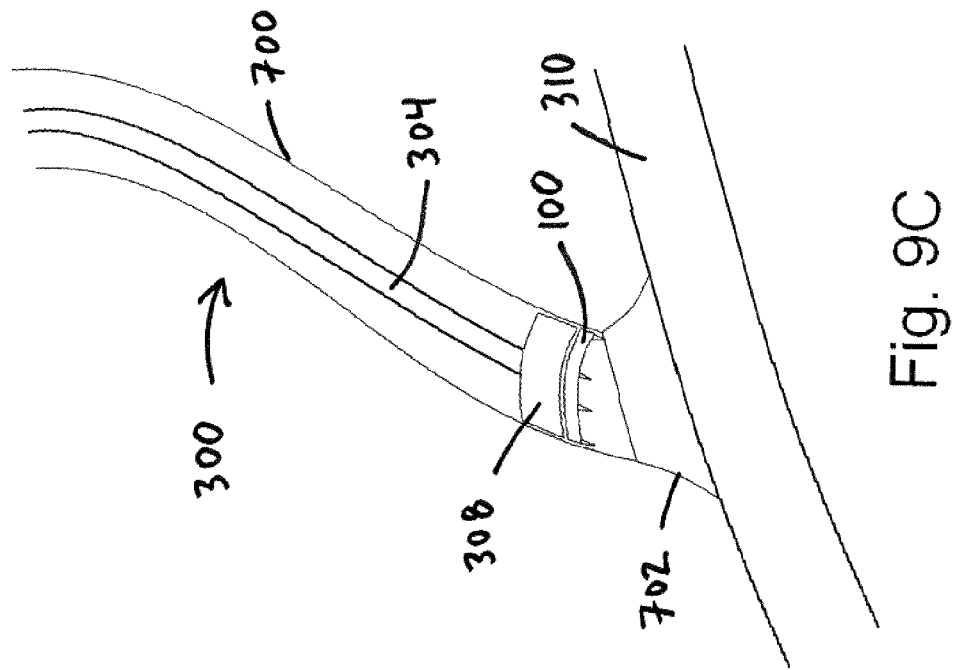
Fig. 9C
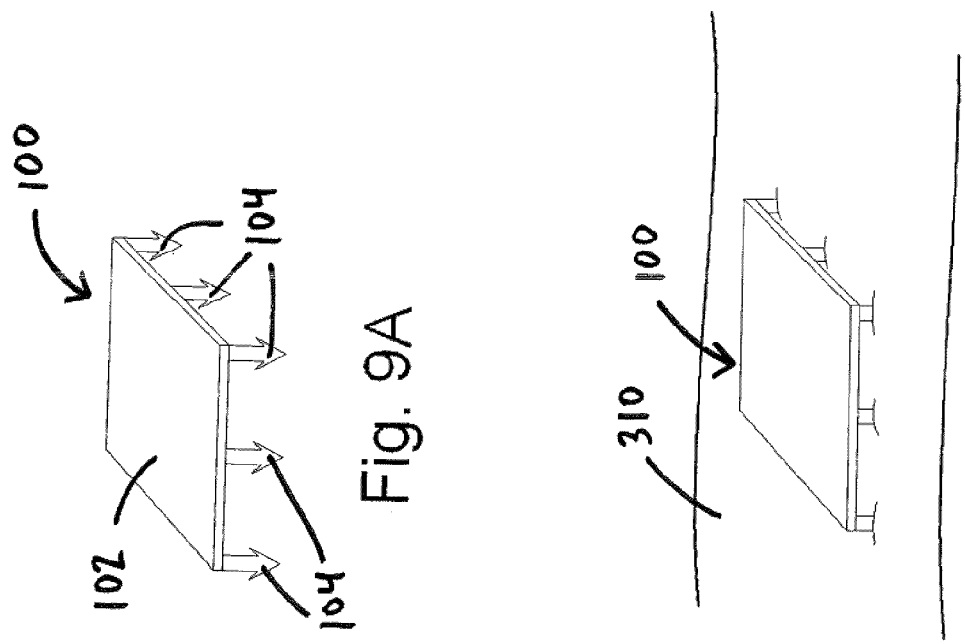
Fig. 9A
Fig. 9B

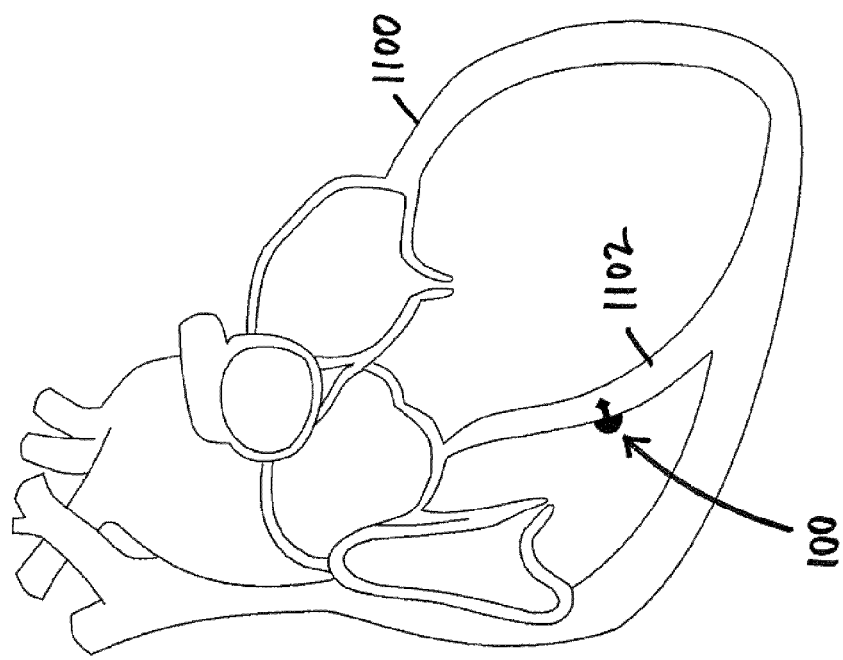
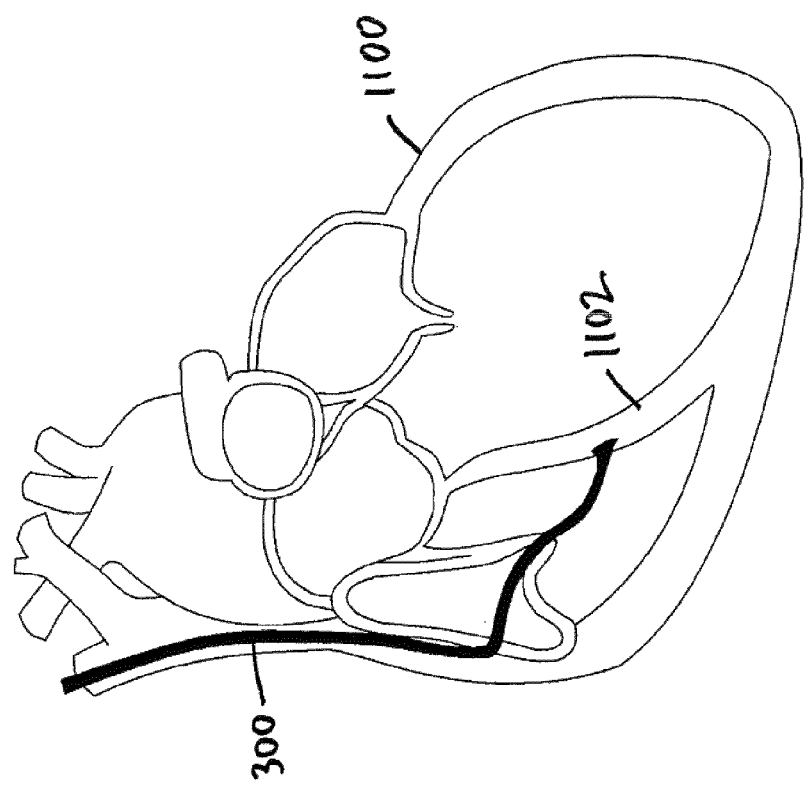

SYSTEMS, DEVICES, AND METHODS FOR LOCALIZED DRUG DELIVERY

PRIORITY

The present application is related to, claims the priority benefit of, and is a continuation application of, U.S. patent application Ser. No. 12/579,125, filed on Oct. 14, 2009 and issued as U.S. Pat. No. 8,535,260 on Sep. 17, 2013, which is related to, and claims the priority benefit of, U.S. Provisional Patent Application Ser. No. 61/105,510, filed Oct. 15, 2008. The contents of each of these applications and patent are hereby incorporated by reference in their entirety into this disclosure.

BACKGROUND

Medications traditionally have been administered in various ways, including orally, subcutaneously, intramuscularly, or intravenously. Other drug delivery systems include transdermal patches, membrane-encased cells genetically engineered to secrete a desired drug (e.g., nerve growth factor or insulin), and slow-release drug systems. Traditional routes of administration require patients to actively follow dosing instructions, for example, when medication is administered orally, such as an antibiotic, hormone, or vitamin, or when repeated visits to the doctor are necessary because the route of administration is by injection. These methods of administration are especially problematic in cases where the patient is a child, elderly, or where the medication must be administered on a chronic basis. Generally, compliance with taking medication is a problem for many adults as they simply forget to take it as recommended or required.

Transdermal patches are used currently to administer drugs such as hormones, estrogen, nicotine, and nitroglycerin (for angina or chest pain). While such a system has been shown to be effective in certain instances, a drug must penetrate the skin barrier in order to be administered via a transdermal patch. Many drugs cannot be administered in effective amounts transdermally. Other slow-release delivery systems are useful, but they require the removal of the matrix itself after the drug has been completely absorbed. Hence, surgery is required to insert the composition and to remove the exhausted matrix from the patient.

Since the sustained release of biological agents was established several decades ago, the sustained release has been advanced by controlling the diffusion of drugs through polymeric matrices and/or the degradation of these polymers. Recently, drug release in proportion to internal or external stimuli has become recognized, which can be achieved by using stimuli-responsive polymeric materials. Many of these polymers achieve their functions by changes in temperature, pH, glucose concentration, and the release of ribosomal enzymes. Biodegradable polymers have great potential for applications as implantable carriers for drug delivery systems. With an auto-feed-back drug delivery system, several physiological changes in a living body can be utilized as the signal inducing polymer degradation and subsequent drug release.

The sustained delivery of antibiotic pharmaceutical agents is often desirable for the treatment of intractable fungal and bacterial infections. Methods of slow drug release have considerable pharmacodynamic advantages over long-term intravenous drug therapy. The former may result in shorter hospitalizations and greater degrees of compliance, and may eliminate the need for indwelling catheters. Slow drug release is usually achieved either by incorporation of a therapeutic drug into an implantable reservoir or by implantation of biodegradable materials containing the desired drug. The development of biodegradable antimicrobial compounds is particularly appealing for the treatment of postsurgical infections and of focal infections in immuno-compromised patients. Efficacies of slow drug release systems are usually determined by measurement of concentrations of the implanted drug in plasma or by assessment of the underlying disease treated (e.g., improving infection or decrease in the size of cancer, etc.).

For chronic heart problems, slow drug release with therapeutic factors having angiogenic, myogenic, and antiarrhythmic potential is very important. The local drug release avoids using larger concentrations or doses to avoid systemic effects. The disclosure of the present application introduces devices, systems, and methods by which implants (biological, chemical or electrical) can be delivered to a tissue and/or organ to provide long term therapeutics.

BRIEF SUMMARY

In at least one embodiment of a device for localized drug delivery of the present disclosure, the device comprises at least one drug release portion comprising at least one drug to be released over time and a binder intermixed with the at least one drug, wherein the binder is biologically degradable within a mammalian body at a first rate of degradation, and also comprises at least one resorbable anchor portion coupled to the at least one drug release portion, wherein the at least one resorbable anchor portion is biologically degradable within the mammalian body at a second rate of degradation, wherein the second rate of degradation is slower than the first rate of degradation. In an exemplary embodiment, and when the device is anchored to a tissue or organ within the mammalian body, as the binder degrades and the at least one drug is released into the mammalian body, the at least one resorbable anchor portion maintains its anchored position within the tissue or organ. In another embodiment, wherein when the device is positioned within the mammalian body, as the binder degrades at the first rate of degradation the at least one drug is released into the mammalian body.

In at least one embodiment of a device for localized drug delivery of the present disclosure, the device comprises a configuration selected from the group consisting of a pin configuration, a hook-pin configuration, and a chip configuration. In an additional embodiment, the at least one resorbable anchor portion comprises at least one barb and at least one point-tip. In yet another embodiment, the at least one resorbable anchor portion comprises at least one coil. In at least one embodiment, the tissue or organ within the mammalian body comprises a mammalian heart.

In at least one embodiment of a system for localized drug delivery of the present disclosure, the system comprises a tube having a proximal end and a distal end, the tube defining a first opening at the proximal end and a second opening at the distal end, the tube sized and shaped to facilitate placement of a resorbable device within a mammalian body by delivering the resorbable device from the second opening of the tube to a location within the mammalian body, and the resorbable device comprising at least one drug release portion and at least one resorbable anchor portion intermixed with the at least one drug release portion. In another embodiment, the system further comprises a shaft positioned within the tube, the shaft having a longitudinal axis, a proximal end, and a distal end, wherein the shaft is operable to facilitate placement of the resorbable device within the mammalian body. In yet another embodiment, the system further comprises an embolus positioned at or near the distal end of the shaft, wherein the embolus is sized and shaped to facilitate placement of the resorbable device within the mammalian body. In an additional embodiment, the shaft is rotatable about its longitudinal axis, and wherein the rotation of the shaft is operable to facilitate placement of the resorbable device within the mammalian body.

In at least one embodiment of a system for localized drug delivery of the present disclosure, the system further comprises a spring positioned at or near the distal end of the shaft between the shaft and the embolus, the spring capable to facilitate placement of the resorbable device within the mammalian body. In another embodiment, the system further comprises an embolus positioned at or near the distal end of the shaft, wherein the embolus is sized and shaped to facilitate placement of the resorbable device within the mammalian body. In an additional embodiment, the introduction of a gas at or near the proximal end of the tube facilitates placement of the resorbable device within the mammalian body.

In at least one embodiment of a system for localized drug delivery of the present disclosure, the tube comprises an engagement catheter. In at least one embodiment, the engagement catheter comprises a suction engagement steering catheter. In another embodiment, the suction engagement steering catheter comprises a skirt positioned at the distal end of the suction engagement steering catheter, the skirt operable to reversibly engage a tissue or organ within the mammalian body to facilitate placement of the resorbable device within the mammalian body. In at least one embodiment, the at least one drug release portion comprises at least one drug to be released over time and a binder intermixed with the at least one drug, the binder biologically degradable within a mammalian body at a first rate of degradation, and wherein the at least one resorbable anchor portion is biologically degradable within the mammalian body at a second rate of degradation, the second rate of degradation being slower than the first rate of degradation.

In at least one embodiment of a method for localized drug delivery of the present disclosure, the method comprises the step of positioning a resorbable device of the present disclosure within a mammalian body, wherein the resorbable device comprises at least one drug release portion comprising at least one drug to be released over time and a binder intermixed with the at least one drug, and further comprising at least one resorbable anchor portion coupled to the at least one drug release portion. In at least one embodiment, the step of positioning the resorbable device within the mammalian body comprises the steps of placing the resorbable device within a tube, introducing the tube within the mammalian body at or near a tissue or organ within the mammalian body, and anchoring the resorbable device to the tissue or organ. In another embodiment, the step of anchoring the resorbable device to the tissue or organ is performed using a shaft positioned within the tube. In yet another embodiment, the step of anchoring the resorbable device to the tissue or organ is performed using a gas from a gas source introduced into the tube to facilitate placement of the resorbable device. In an additional embodiment, the tissue or organ within the mammalian body comprises a mammalian heart.

BRIEF DESCRIPTION OF THE DRAWINGS

FIG. 1A shows a block diagram of an exemplary composition of at least one embodiment of a resorbable device according to the present application;

FIG. 1B shows a block diagram of another exemplary composition of a resorbable device according to the present application;

FIGS. 2A and 2B show exemplary embodiments of resorbable devices according to the present application having a pin configuration;

FIG. 2C shows an exemplary embodiment of a resorbable device according to the present application having a hook-pin configuration;

FIG. 2D shows an exemplary embodiment of a resorbable device according to the present application having a chip configuration;

FIG. 2E shows an exemplary embodiment of a resorbable device according to the present application having a coiled resorbable anchor portion;

FIGS. 3A and 3B show cross-sectional views of an exemplary embodiment of a delivery system according to the present application having a tube, a shaft, a spring, and an embolus, wherein the delivery system is used to position a resorbable device at a tissue and/or organ;

FIG. 3C shows a cross-sectional views of an exemplary embodiment of a delivery system according to the present application having a tube, a shaft, a spring, and an embolus, wherein the delivery system has a notable curvature useful to facilitate positioning a resorbable device at a tissue and/or organ;

FIGS. 4A and 4B show cross-sectional views of an exemplary embodiment of a delivery system according to the present application having a tube, a shaft, and an embolus, wherein the delivery system is used to position a resorbable device at a tissue and/or organ;

FIG. 9A shows an exemplary embodiment of a resorbable device according to the present application having a chip configuration;

FIG. 9B shows an exemplary embodiment of a resorbable device according to the present application having a chip configuration positioned at a tissue and/or organ;

FIG. 9C shows a cross-sectional view of an exemplary embodiment of a delivery system according to the present application having a tube, a shaft, and an embolus, wherein the delivery system is used to position a resorbable device having a chip configuration at a tissue and/or organ;

FIG. 11A shows an exemplary embodiment of a delivery system according to the present application used to position a resorbable device within a heart;

FIG. 11B shows an exemplary embodiment of a resorbable device according to the present application positioned at a heart septum.

DETAILED DESCRIPTION

Figure 5B:
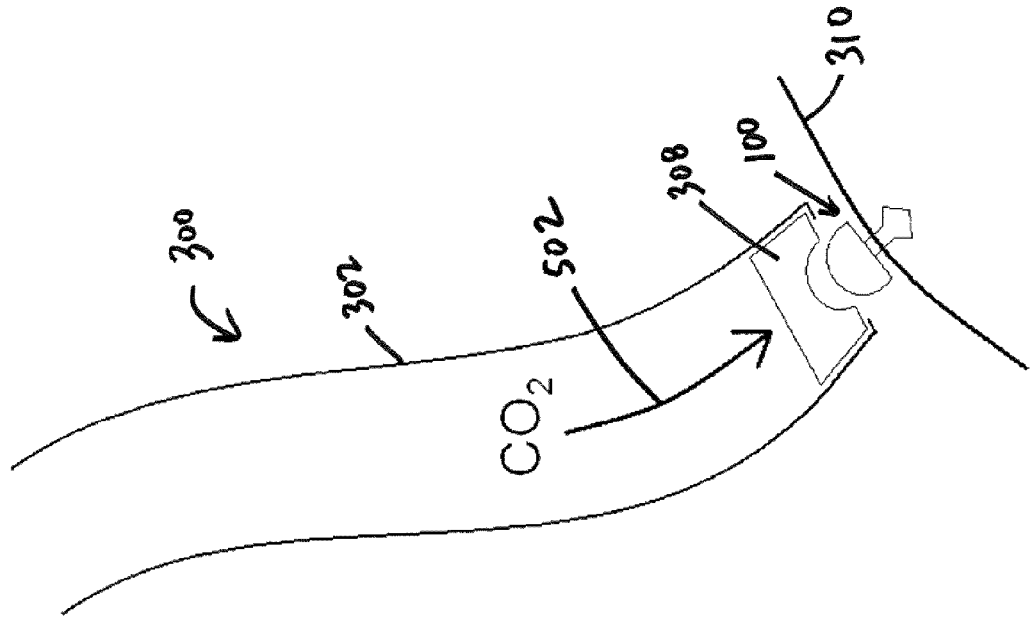
FIGS. 5A and 5B show cross-sectional views of an exemplary embodiment of a delivery system according to the present application having a tube and an embolus, wherein the delivery system is used to position a resorbable device at a tissue and/or organ using a gas.

The disclosure of the present application provides various devices and systems for localized drug delivery and methods for using the same. For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

The devices, systems, and methods of the disclosure of the present application allow patients to receive medications in a slow-release, self-absorbing/resorbable form at various time intervals, for example, from days to weeks to months. In at least one embodiment, one or more drugs may be released at intervals of about one month, depending on the rate of absorption of the associated matrix. Exemplary devices of the present disclosure may be used as an implantable, slow-release, self-absorbing pharmaceutical composition containing one or more active agents in combination with a biologically-compatible, self-absorbing matrix useful to deliver the pharmaceutical composition to the bloodstream and/or directly to a bodily tissue and/or organ. Such devices may also be a pacemaker-type device or similar electronics to transmit electrical therapy (pacing, resynchronization or defibrillation) chronically and as needed. As referenced herein, the terms "self-absorbing" and "resorbable" refer to properties of various devices which are biologically absorbable within a mammalian body as described in further detail herein.

The disclosure of the present application discloses devices providing an implantable pharmaceutical composition containing the active substance in a biologically-compatible, self-absorbing matrix. Further, the disclosure of the present application provides an implantation device for implanting such pharmaceutical compositions in various bodily tissues including, for example, myocardial muscle. In at least some embodiments of a device of the disclosure of the present application, the device comprises a slow-release, self-absorbing, pharmaceutical composition containing one or more active agents in combination with a biologically-compatible, self-absorbing matrix to treat patients with congestive heart failure (using, for example, various beta blockers, anticalcic agents, and/or cardiotonic drugs), coronary vasodilators in patients with refractory angina, anti-arrhythmic drugs, pulmonary vasodilators (PG1) to treat primary pulmonary hypertension, anticoagulation therapy (using, for example, fibrinolitics and/or antiadhesive platelets treatment), antibiotics for chronic fungal or bacterial cardiac infections or pulmonary infections (e.g., cystic fibrosis lung disease), and anti-rejection drugs (heart transplants), for example.

In addition to the foregoing, there are particular sites within the myocardium which may benefit from local drug release therapy. Examples include ischemic sites and arrhythmogenic sites for localized use of fibrinolitic or anticoagulation therapy or vasodilators. The local delivery of agents within such tissues will minimize the dilution of agents and decrease the possibility of the agents being delivered to inappropriate sites. This localized delivery is important, for example, for antiarrhythmic agents whose pro-arrhythmia systemic effects have been well recognized.

In at least one embodiment of a system and/or device of the present application, the system and/or device comprises an engagement-suction catheter that can deliver drugs to specific and precise "target" within the heart or other organ(s) and/or tissue(s). The disclosure of the present application is intended for minimally invasive delivery of agents for the treatment of medical conditions, for example, those conditions in the heart or adjacent veins and arteries where precision injection of genes or other agents is required in the treatment of the patient. Available epidemiologic, pharmacologic, and clinico-therapeutic evidence demonstrates how the chronobiologic approach to ischemic heart disease can contribute new insight and opportunities to improve drug design and drug delivery to enhance therapeutic outcomes. In at least one embodiment of a device, system, or method of the present disclosure, an objective is to make drug delivery to the endocardial surface of the heart very specific and precise.

At least one embodiment of a device of the present application is shown in the block diagram of FIG. 1A. As shown in FIG. 1A, an exemplary device (generally referred to herein as a resorbable device 100) comprises at least two components, namely a drug release portion 102 and a resorbable anchor portion 104. Drug release portion 102, in order to facilitate the delivery of a drug over time as described herein, is configured so that a drug is capable of at least localized delivery within a patient's body after resorbable device 100 has been implanted therein. For purposes of the present disclosure, a "drug" shall mean at least one of any number of therapeutics, pharmaceuticals, vitamins, antibiotics, hormones, and the like. The disclosure of the present application does not intend for the term "drug" to be limited to, for example, a prescription medication.

Drug release portion 102 may comprise any number of configurations for the release of a drug over time. For example, drug release portion 102 may comprise a drug combined with a binder/filler, whereby as the binder/filler breaks down over time within the body, the drug is released over time. Drug release portion 102 may comprise, for example, a biologically-compatible, resorbable matrix that biodegrades over time once positioned within a patient's body. Drug release portion 102 may also comprise a drug positioned within a biodegradable shell, wherein the drug may be released within a body as the biodegradable shell degrades, is absorbed, or is digested within a body.

In the exemplary embodiment of a resorbable device 100 shown in the block diagram of FIG. 1B, resorbable device 100 comprises a drug release portion 102, wherein drug release portion 102 comprises a drug portion 106 and a binder 108 either bound to and/or around drug portion 106, whereby the use of the binder 108 allows the drug within drug portion 106 to be released, for example, within the blood stream, as binder 108 breaks down within the body. In such an exemplary embodiment, drug portion 106 and binder 108 are intermixed with one another to facilitate the time-release of drug portion 106 as referenced herein.

To facilitate the "anchoring" of resorbable device 100 within the body, resorbable device 100 comprises a resorbable anchor portion 104. Exemplary embodiments of resorbable devices 100 of the disclosure of the present application are shown FIGS. 2A-2E. In the exemplary embodiment of a resorbable device 100 shown in FIG. 2A, resorbable device 100 has a "pin" configuration, whereby the pin 200 is sized and shaped for placement within the body in, for example, cardiac tissue or one or more other bodily organs, such as digestive, respiratory, and/or urinary tracts. In such an embodiment, and as with additional embodiments referenced herein, the pin 200 (or other form of a resorbable device 100) may be anchored within the body for a period of time to allow for at least some drug delivery over time from the drug release portion 102. In the exemplary embodiment shown in FIG. 2A, resorbable device 100 comprises a partially-round drug release portion 102 and a resorbable anchor portion 104 having barbs 202 to facilitate anchoring within a body as described herein. FIG. 2B shows another exemplary embodiment of a resorbable device 100 in having a pin 200 configuration, wherein the drug release portion 102 is substantially round and wherein the pin 200 has a point tip 204 allowing resorbable device to be positioned within a body. As referenced herein, various additional embodiments and/or configurations of pins 200 may comprise any number of shapes, components and/or features, including, but not limited to, barbs 202 and/or point tip 204.

Figure 8C:
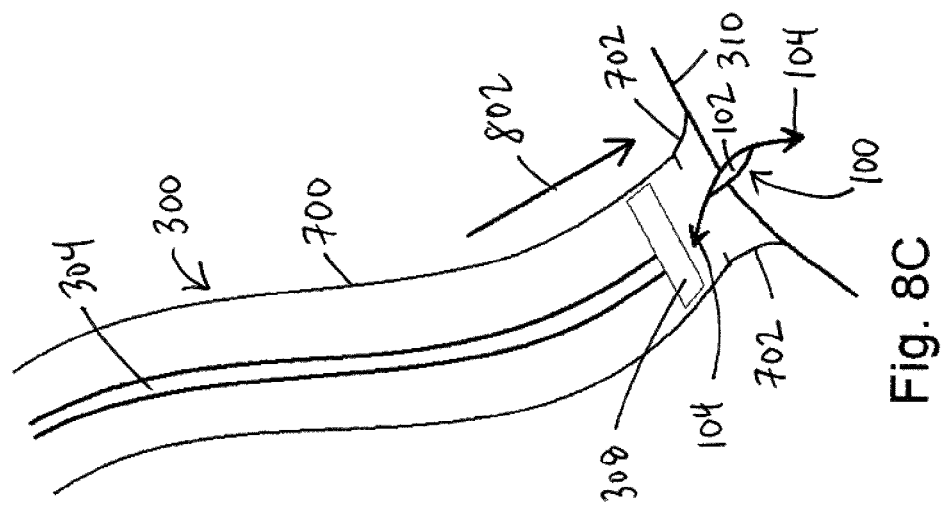
FIGS. 8B and 8C show cross-sectional views of an exemplary embodiment of a delivery system according to the present application having a tube, a shaft, and an embolus, wherein the delivery system is used to position a resorbable device having a hook-pin configuration at a tissue and/or organ.
Figure 8B:
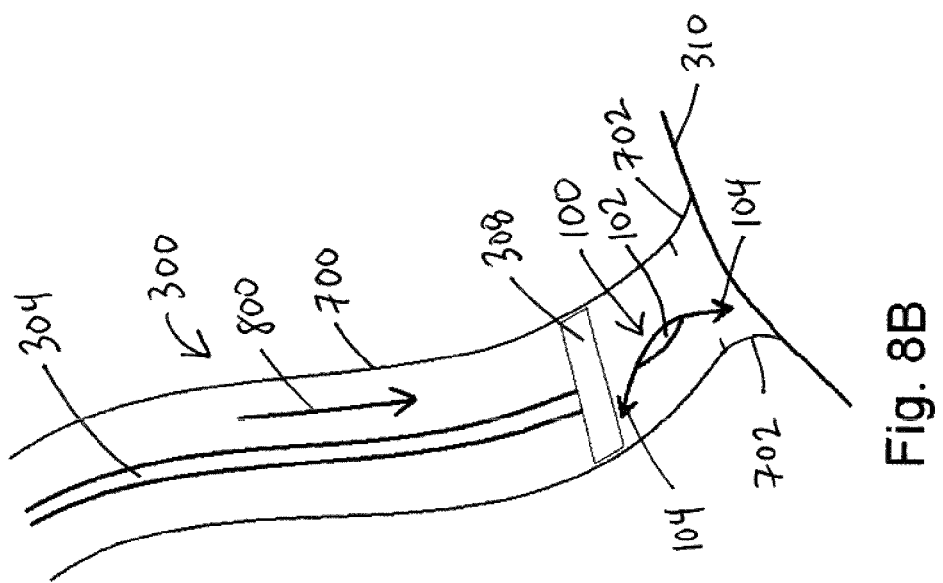

Additional exemplary embodiments of a resorbable device 100 of the disclosure of the present application are shown in FIGS. 2C-2E. FIG. 2C shows an embodiment of a resorbable device 100 with a natively curved configuration, whereby resorbable device 100 may be anchored within a body using two resorbable anchor portions 104 to allow drug release portion 102 to release drug over time. Anchor portion 104 may comprise any number of attributes as referenced herein in connection with other anchor portions 104, including, but not limited to, barbs 202 and/or point tip 204. Placement of such an embodiment within a body is shown in FIGS. 8B and 8C.

FIG. 2D shows an embodiment of a resorbable device 100 in "chip" form, wherein the drug release portion 102 comprises a chip 206, and wherein one or more resorbable anchor portions 104 facilitate the anchoring of resorbable device 100 within a body. Chip 206 may also comprise, for example, a microchip and/or one or more other mechanisms to facilitate a programmed delivery of drug over time. In addition, a resorbable device 100 having a chip 206 configuration, or another configuration of a resorbable device 100 of the present disclosure sized and shaped to allow for the positioning of a microchip thereon, may be or function similar to various electrical stimulating pacemakers or other types of electronics to transmit electrical therapy chronically and/or as needed. For example, and in at least one embodiment of a resorbable device 100 of the present disclosure, resorbable device 100 comprises a chip 206 configuration as shown in FIG. 2D, wherein the chip 206 comprises a microchip.

Figure 6B:
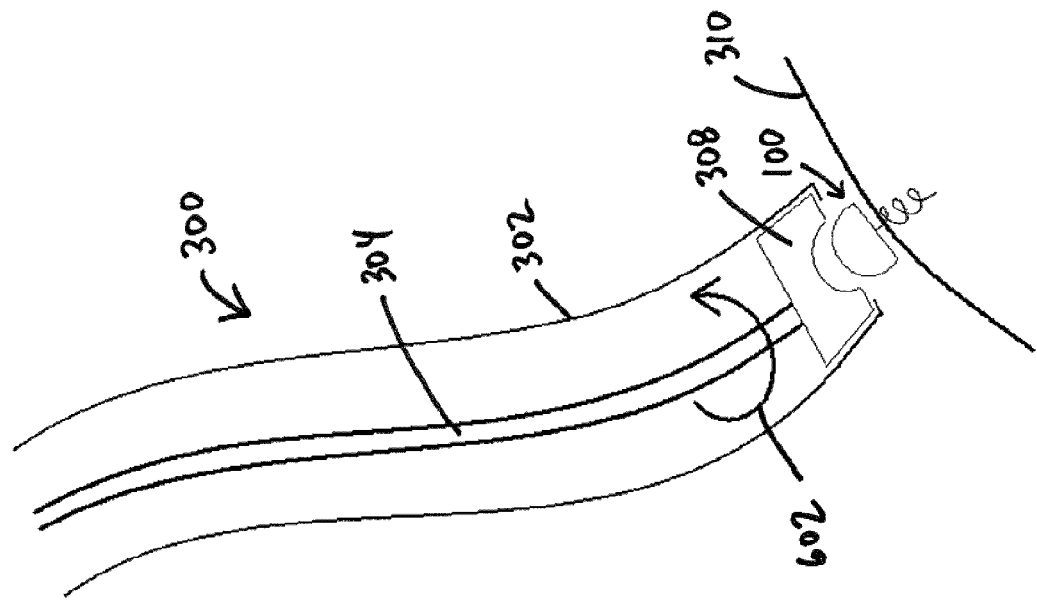
FIGS. 6A and 6B show cross-sectional views of an exemplary embodiment of a delivery system according to the present application having a tube, a shaft, and an embolus, wherein the delivery system is used to position a resorbable device at a tissue and/or organ by rotating the shaft about its longitudinal axis.
Figure 6A:
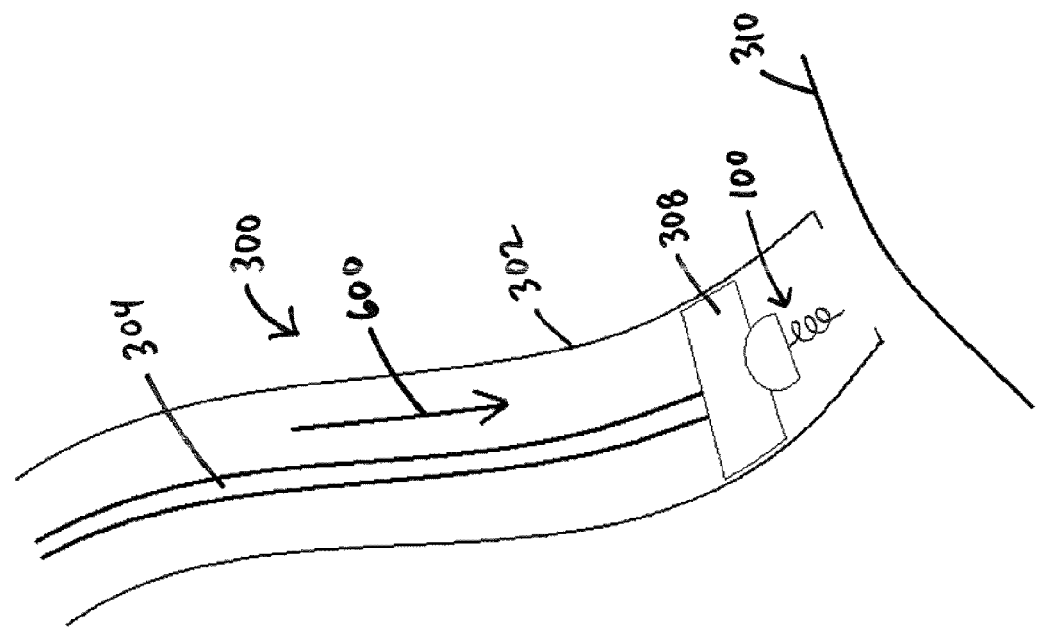

FIG. 2E shows an exemplary embodiment of a resorbable device 100 whereby the resorbable anchor portion 104 comprises a screw-like configuration (a coil screw 208 with a single or double helix, for example), whereby the resorbable device 100 may be screwed into position as described in FIGS. 6A and 6B. Additional embodiments and configurations of resorbable device 100 comprising a drug release portion 102 and a resorbable anchor portion 104 as referenced herein are contemplated to be within the scope of the present application.

A cross-sectional view of an exemplary system for positioning a resorbable device within a body is shown in FIGS. 3A and 3B. As shown in FIG. 3A, exemplary delivery system 300 comprises a delivery tube 302 and a shaft 304 slidingly engaged within delivery tube 302. Shaft 304, when moved in a direction as shown by arrow 314 in FIG. 3B, exerts pressure on a spring 306 which, in turn, exerts a pressure on an embolus 308 to facilitate delivery of resorbable device 100 (shown having a pin 200 configuration in FIGS. 3A and 3B). As shown in FIG. 3B, when shaft 304 moves in the direction shown by arrow 314, resorbable device 100 may be implanted into tissue and/or organ 310, with the surface of tissue and/or organ 310 shown in FIGS. 3A and 3B. In an embodiment of a resorbable device 100 wherein resorbable device 100 comprises barbs 202 and/or a point tip 204 (as shown in FIGS. 2A, 2C, and 2D), point tip 204 may puncture tissue and/or organ 310 to facilitate anchoring of resorbable device 100 therein, and/or barbs 202 may physically engage tissue and/or organ 310 to prohibit removal of resorbable device 100 after it is anchored.

As shaft 304 slides within tube 302, embolus 308 facilitates the delivery of resorbable device 100 as shown in FIG. 3B. Embolus 308 may be prevented from exiting tube 302 by, for example, the use of one or more embolus stop bars 312 as shown in FIGS. 3A and 3B. Furthermore, embolus 308 (and/or portions of shaft 304 as described below) may be sized and shaped so that a resorbable device 100 may be removably engaged thereto and subsequently delivered to a target area within a body as described herein.

Exemplary resorbable devices 100 of the disclosure of the present application may be positioned in or onto any number of tissues and/or organs 310, including, but not limited to, heart tissue, muscle, the brain, and the lungs. Such resorbable devices 100, when positioned within a tissue and/or organ 310, should not be positioned so deeply as to cause potential hemorrhage and/or filtration of a vascular bed. In at least one embodiment, resorbable devices 100 may be delivered to a target tissue and/or organs using any number of delivery systems 300 of the present disclosure, with the various delivery systems 300 configured for a particular application. For example, an exemplary delivery system 300, such as delivery system 300 shown in FIGS. 3A and 3B, may be used to deliver resorbable devices 100 to a tissue or organ having a surface relatively perpendicular to the direction of entry of the delivery system 300. As shown in FIG. 3A, for example, the distal end 316 of delivery system 300 is relatively perpendicular to tissue and/or organ 310, whereby such a configuration of delivery system 300 is suitable to deliver a resorbable device 100 of the present disclosure. In at least another embodiment, and as shown in the cross-sectional view of an exemplary system for positioning a resorbable device within a body shown in FIG. 3C, delivery system 300 has a notable curvature to facilitate delivery of resorbable device 100 to a tissue and/or organ 310 relatively parallel to the direction of entry of delivery system 300 into the body.

Additional cross-sectional views of exemplary embodiments of delivery systems 300 of the disclosure of the present application are shown in FIGS. 4A and 4B. As shown in the embodiment shown in FIG. 4A, delivery system 300 comprises tube 302, shaft 304, and embolus 308. In this exemplary embodiment, delivery system 300 does not comprise a spring 306, and use of the system (by sliding shaft 304 in the direction of arrow 400 shown in FIG. 4B towards the distal end of tube 302) delivers a resorbable device 100 as previously described herein. In the exemplary embodiment shown in FIG. 4B, delivery system 300 comprises a tube 302 and a shaft 304, whereby resorbable device 100 may be positioned using only shaft 304. The embodiments of delivery system 300 as shown in FIGS. 3A-4B are exemplary in nature, and other mechanical embodiments of delivery systems 300 operable to deliver resorbable devices 100 as referenced herein are considered to be within the scope of the present application.

Figure 5A:
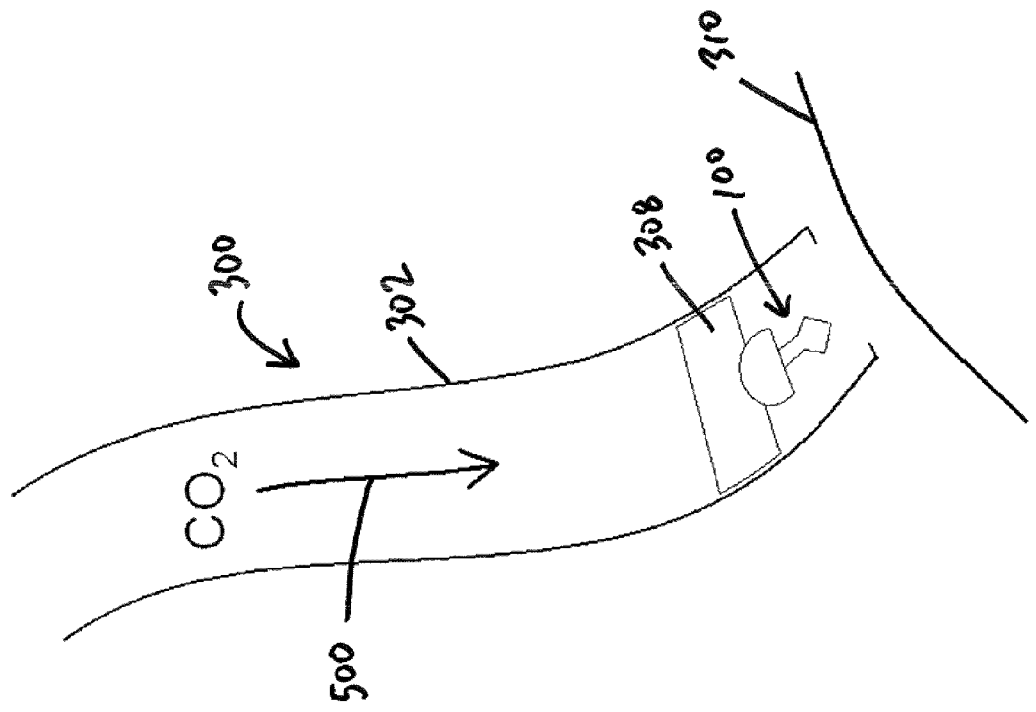

An cross-sectional view of an exemplary embodiment of a delivery system 300 of the disclosure of the present application utilizing pressurized gas is shown in FIGS. 5A and 5B. As shown in FIGS. 5A and 5B, delivery system 300 comprises a tube 302, an embolus 308, and a resorbable device 100. The delivery of a gas from a gas source (not shown) may, as shown in FIG. 5B, cause embolus 308 and resorbable device 100 to move in the direction shown by arrows 500, 502 so that resorbable device 100 may be positioned within a tissue and/or organ 310. Carbon dioxide ($CO_2$) is shown as being the gas in this exemplary embodiment, but any number of various gases may be used to accomplish the same. Additionally, one or more fluids (water, saline, etc.) may be used either in place of, or in addition to, one or more gases to facilitate delivery of resorbable device 100.

A cross-sectional view of an additional embodiment of a delivery system 300 of the disclosure of the present application is shown in FIGS. 6A and 6B. As shown in FIGS. 6A and 6B, delivery system 300 comprises a tube 302 and a shaft 304 where shaft 304 is capable of rotation about its longitudinal axis as shown in FIG. 6B. Shaft 304 is either permanently or removably coupled to embolus 308 and is sized and shaped to facilitate delivery of resorbable device 100. Resorbable device 100 may be positioned at or near a tissue and/or organ 310 by moving shaft 304 in a direction of arrow 600 shown in FIG. 6A. When resorbable device is positioned at or near tissue and/or organ 310, shaft 304 may be rotated about its longitudinal axis as shown by arrow 602 in FIG. 6B, causing resorbable device 100 (having a resorbable anchor portion 104 comprising a screw-like configuration as shown, for example, in FIG. 2E) to be screwed into position within tissue and/or organ 310.

Figure 7:
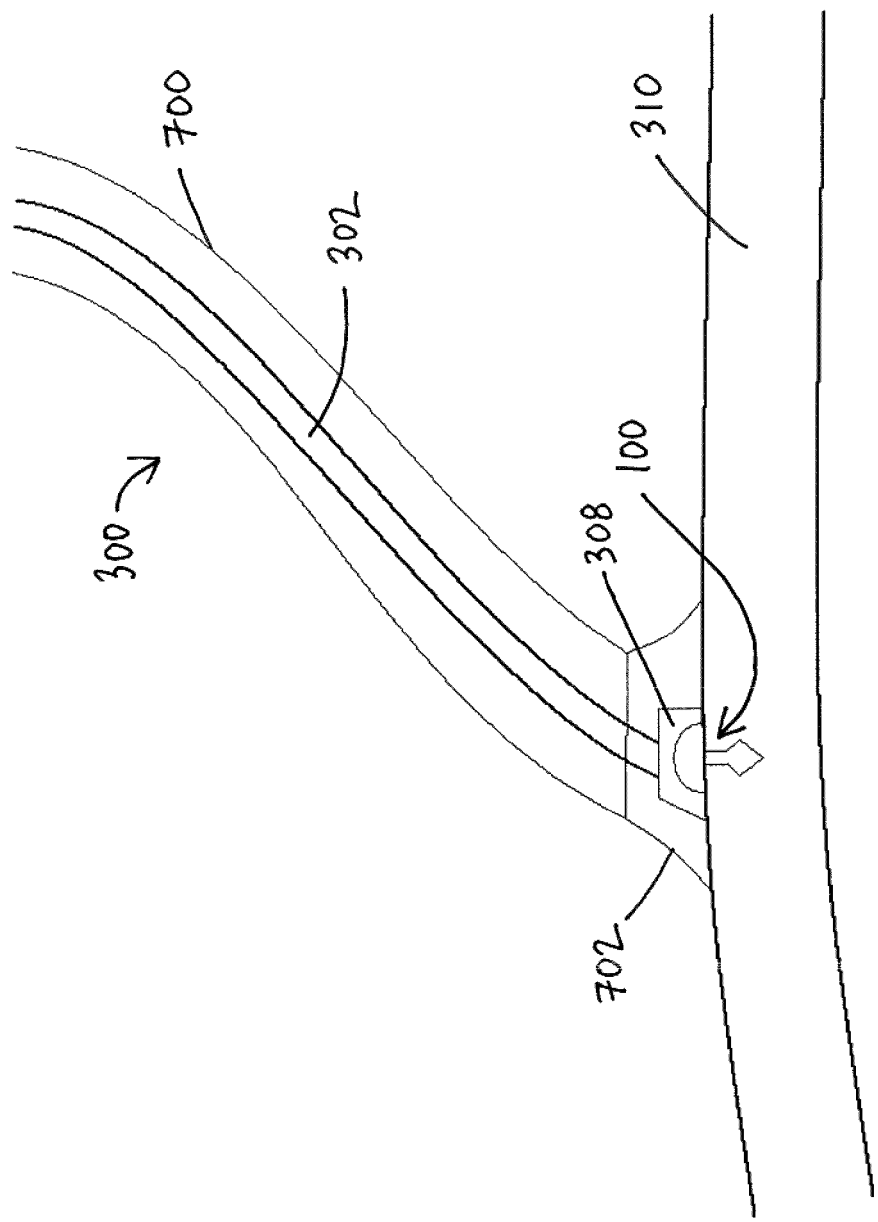
FIG. 7 shows a cross-sectional view of an exemplary embodiment of a delivery system according to the present application having an engagement catheter with an optional skirt, a shaft, and an embolus, wherein the delivery system is used to position a resorbable device at a tissue and/or organ.

FIG. 7 shows a cross-sectional view of an embodiment of a delivery system 300 of the disclosure of the present application wherein suction facilitates the delivery of resorbable device 100. As shown in the exemplary embodiment shown in FIG. 7, delivery system 300 comprises an engagement catheter 700 and shaft 304 positioned therein, wherein the movement of shaft 304 within engagement catheter 700, similar to the movement of shaft 304 within tube 302 in other embodiments referenced herein, facilitates the positioning of resorbable device 100 within a target tissue and/or organ 310. Engagement catheter 700 may comprise any number of engagement catheters capable of reversibly attaching to a target tissue and/or organ 310 as shown in FIG. 7. In at least one preferred embodiment, engagement catheter 700 comprises a suction engagement steering catheter, wherein said catheter may be inserted into a body to a particular target site for delivery of resorbable device 100. In such an embodiment, engagement catheter 700 may be referred to generally as a delivery catheter if it facilitates the placement, or delivery, of a resorbable device 100.

In the exemplary embodiment shown in FIG. 7, delivery system 300 further comprises an embolus 308 sized and shaped to facilitate the delivery of resorbable device 100. In addition, and as shown in this exemplary embodiment, engagement catheter 700 may optionally comprise a skirt 702 coupled to the distal end of engagement catheter 700, allowing engagement catheter 700 to engage a larger surface area of a tissue and/or organ 310 as would otherwise be possible without such a skirt 702. Engagement catheter 700 may reversibly attach to a tissue and/or organ 310 using suction from a suction source (not shown) operably coupled to the engagement catheter 700 at or near the proximal end of the engagement catheter 700.

Figure 8A:
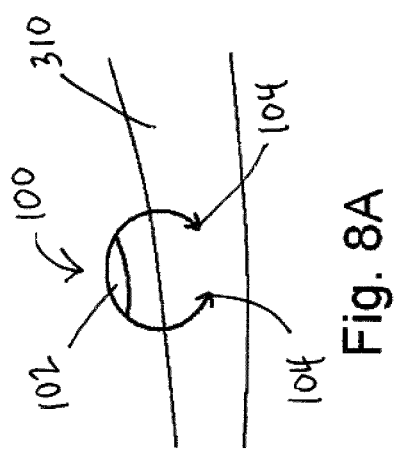
FIG. 8A shows an exemplary embodiment of a resorbable device of the present application having a hook-pin configuration positioned at a tissue and/or organ.

Another cross-sectional view of an embodiment of a delivery system 300 of the disclosure of the present application is shown in FIGS. 8B and 8C. As shown in FIGS. 8B and 8C, delivery system 300 comprises an engagement catheter 700 (shown with an optional skirt 702), a shaft 304, and an embolus 308, whereby delivery system 300 is operable to deliver resorbable device 100 to a target tissue and/or organ 310 in the direction of arrows 800, 802. In the exemplary embodiment shown in FIGS. 8A-8C, resorbable device 100 has a hook-pin configuration (similar to the configuration shown in FIG. 2C), and in this particular embodiment, resorbable device 100 comprises a "memory" whereby its natural/native configuration is a hook configuration (as shown in FIG. 8A), which can be temporarily bent into a relatively open position for implantation as shown in FIGS. 8B and 8C). Materials having such a memory suitable for various resorbable devices of the present disclosure include, but are not limited to, polymers derived from polylactic-co-glycolic acid) (PLGA) including various copolymers, graft copolymers, interpenetrating networks (IPNS), dipalmitylphosphatidylcholine, chondroitin sulfate A, polylactic acid) (PLA), and PLGA itself. In practice, such an embodiment of resorbable device 100 may be bent open to fit within engagement catheter 700, and pushed into position using shaft 304 and/or embolus 308. After resorbable device 100 has engaged tissue and/or organ 310 as shown in FIG. 8C (by way of a resorbable anchor portion 104), removal of delivery system 300 away from resorbable device 100 may allow resorbable device 100, as shown in the embodiment shown in FIG. 8A, to bend back into its natural/native configuration, allowing a second resorbable anchor portion 104 to engage tissue and/or organ 310. Such a delivery may then allow drug release portion 102 to deliver a drug over time as described herein.

FIG. 9C shows a cross-sectional view of an embodiment of a delivery system 300 of the disclosure of the present application used to position a resorbable device 100 of the present application having a chip configuration as shown in FIGS. 9A and 9B. As shown in the exemplary embodiment shown in FIG. 9C, delivery system 300 comprises an engagement catheter 700 having an optional skirt 702, a shaft 304, and an optional embolus 308, whereby delivery system 300 is used to position a resorbable device 100 upon a tissue and/or organ 310. When shaft 304 has been extended toward the distal end of engagement catheter 700, resorbable device 100 may be positioned at tissue and/or organ 310 as shown in FIG. 9B, whereby drug from the drug release portion 102 may be delivered over time. In the embodiment of resorbable device 100 shown in FIGS. 9A-9C, resorbable device 100 comprises several resorbable anchor portions 104, noting that various embodiments of resorbable devices 100 of the disclosure of the present application may have one or more resorbable anchor positions 104.

Figure 10A:
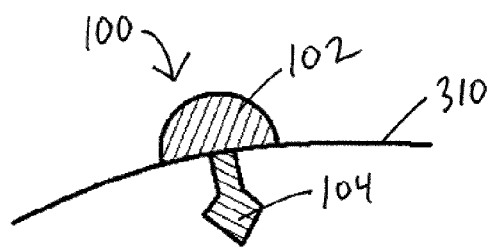
FIG. 10A shows an exemplary embodiment of a resorbable device according to the present application positioned at a tissue and/or organ.
Figure 10B:
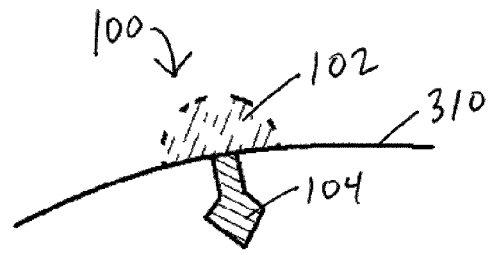
FIG. 10B shows an exemplary embodiment of a resorbable device according to the present application positioned at a tissue and/or organ wherein the drug release portion of the resorbable device has start to biologically degrade allowing the release of drug.
Figure 10C:
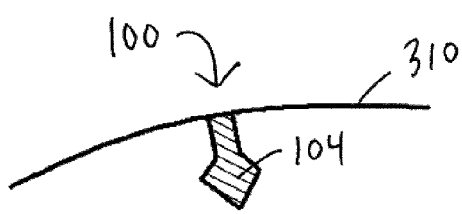
FIG. 10C shows an exemplary embodiment of a resorbable device according to the present application positioned at a tissue and/or organ wherein the drug release portion has completely biologically degraded.
Figure 10D:
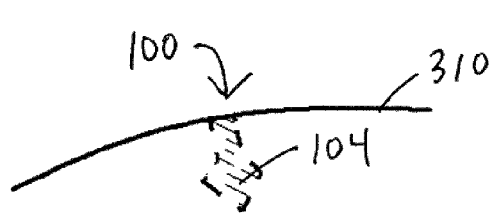
FIG. 10D shows an exemplary embodiment of a resorbable device according to the present application positioned at a tissue and/or organ wherein the resorbable anchor portion of the resorbable device has start to biologically degrade.
Figure 10E:
FIG. 10E shows an exemplary embodiment of a resorbable device according to the present application positioned at a tissue and/or organ wherein the drug release portion and the resorbable anchor portion have both completely biologically degraded.

FIG. 10A-10E show the resorption over time of an exemplary resorbable device 100 of the disclosure of the present application. FIG. 10A shows an exemplary embodiment of a resorbable device 100 having a drug release portion 102 positioned outside of a tissue and/or organ 310 and a resorbable anchor portion 104 positioned within a tissue and/or organ 310. Over time, drug release portion 102 will begin to degrade and deliver drug present within drug release portion 102 as shown in FIG. 10B. FIG. 10C shows an embodiment of resorbable device 100 whereby drug release portion 102 has completely been absorbed by the body and all drug within drug release portion 102 has been released. In at least one exemplary embodiment as shown in FIG. 10D, after drug release portion 102 has either partially or completely delivered the drug, resorbable anchor portion 104 will begin to degrade, and as shown in FIG. 10E, no portion of resorbable device 100 remains after drug release portion 102 and resorbable anchor portion 104 has been absorbed/degraded by the body.

Figure 12:
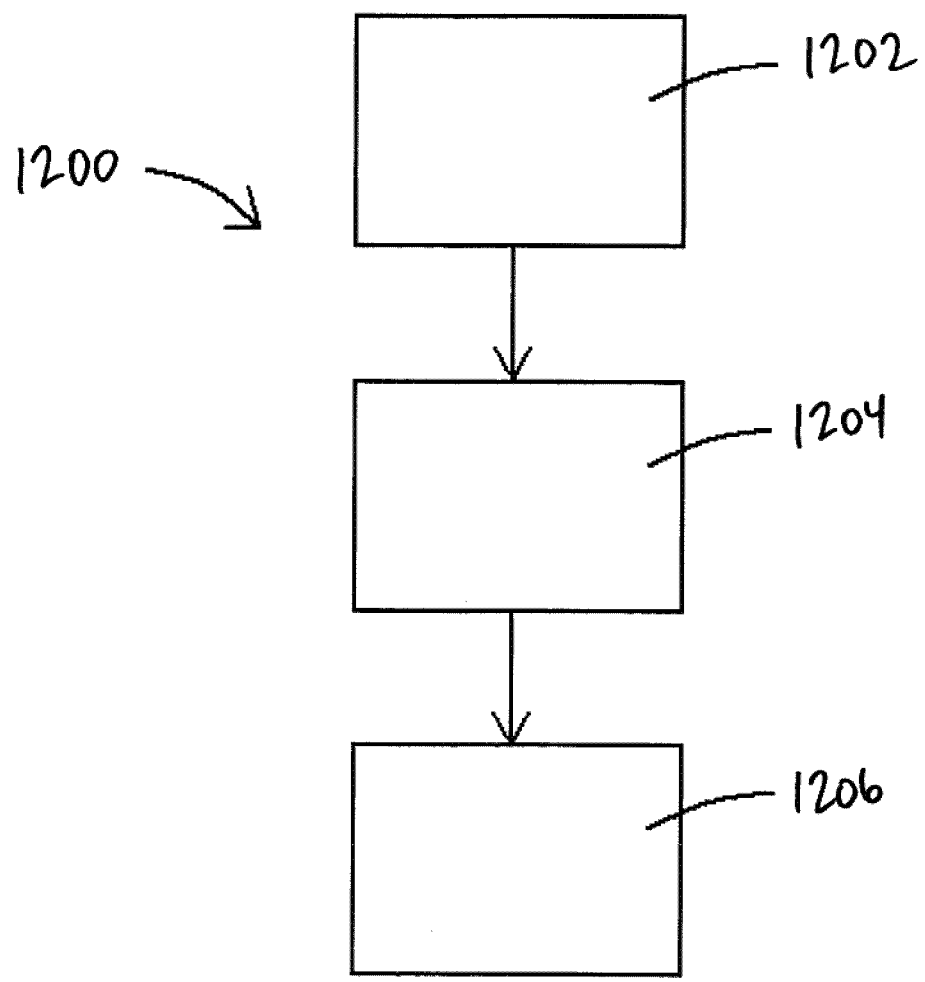
FIG. 12 shows a block diagram of an exemplary method of positioning a resorbable device within a body according to the present application.

FIGS. 11A and 11B show how an exemplary embodiment of a delivery system 300 of the disclosure of the present application may be used to deliver a resorbable device 100 of the present application to a septal wall of a heart. As shown in FIG. 11A and with the exemplary method steps identified in the method block diagram shown in FIG. 12, delivery system 300 may be positioned within a blood vessel leading to a heart 1100 (an exemplary tissue and/or organ 310), further accessing heart 1100 (via the pericardial space of the heart 1100, for example), to deliver resorbable device 100 as described herein. Prior to introducing the delivery system 300 within the body at or near a target tissue or organ (introduction step 1204), an exemplary method 1200 of the present application comprises the step of placing the resorbable device 100 within a delivery tube 302 of delivery system 300 (placement step 1202). FIG. 11B shows an embodiment of a resorbable device 100 positioned within a heart 1100 at the septal wall 1102 of the heart 1100, positioned therein by, for example, performing the step of anchoring the resorbable device to the target tissue or organ (anchoring step 1206). The disclosure of the present application is not intended to be limited to the delivery of only a pin 200 configuration of a resorbable device 100 to the septal wall 1102 of a heart 1100, noting that any number of configurations of a resorbable device 100 of the disclosure of the present application may be positioned within any number of tissues and/or organs 310 within a body as described herein.

While various embodiments of devices, systems, and methods for localized drug delivery have been described in considerable detail herein, the embodiments are merely offered by way of non-limiting examples of the disclosure described herein. It will therefore be understood that various changes and modifications may be made, and equivalents may be substituted for elements thereof, without departing from the scope of the disclosure. Indeed, this disclosure is not intended to be exhaustive or to limit the scope of the disclosure.

Further, in describing representative embodiments, the disclosure may have presented a method and/or process as a particular sequence of steps. However, to the extent that the method or process does not rely on the particular order of steps set forth herein, the method or process should not be limited to the particular sequence of steps described. Other sequences of steps may be possible. Therefore, the particular order of the steps disclosed herein should not be construed as limitations of the present disclosure. In addition, disclosure directed to a method and/or process should not be limited to the performance of their steps in the order written. Such sequences may be varied and still remain within the scope of the present disclosure.

The invention claimed is:

1. A method for localized drug delivery, the method comprising the step of positioning a resorbable device within a pericardial space surrounding a heart of a mammalian body, wherein the resorbable device comprises:
    at least one drug release portion, comprising:
        at least one drug to be released over time, and
        a binder intermixed with the at least one drug, the binder biologically degradable within the mammalian body at a first rate of degradation; and
    at least one resorbable anchor portion forming the device with the at least one drug release portion and configured to actively engage and anchor to a surface of the heart within the mammalian body, the at least one resorbable anchor portion biologically degradable within the mammalian body at a second rate of degradation that is slower than the first rate of degradation.

2. The method of claim 1, wherein the step of positioning the resorbable device within the mammalian body comprises the steps of:
    placing the resorbable device within a tube;
    introducing the tube into the pericardial space; and
    anchoring the resorbable device to the surface of the heart.

3. The method of claim 2, wherein the step of anchoring the resorbable device to the surface of the heart is performed using a shaft positioned within the tube.

4. The method of claim 2, wherein the step of anchoring the resorbable device to the surface of the heart is performed using a gas from a gas source introduced into the tube to facilitate placement of the resorbable device.

5. A device for localized drug delivery, the device comprising:
    at least one drug release portion comprising a binder and at least one drug, the binder biologically degradable within a mammalian body at a first rate of degradation; and
    at least one resorbable anchor portion forming the device with the at least one drug release portion and configured to actively engage and anchor to a surface of a tissue or organ within the mammalian body, the at least one resorbable anchor portion biologically degradable within the mammalian body at a second rate of degradation that is slower than the first rate of degradation.

6. The device of claim 5, wherein when the device is anchored to the surface of the tissue or organ within the mammalian body, the at least one resorbable anchor portion maintains its anchored position within the tissue or organ as the binder initially degrades and the at least one drug is released into the mammalian body.

7. The device of claim 5, wherein when the device is positioned within the mammalian body, the at least one drug is released into the mammalian body as the binder degrades at the first rate of degradation.

8. The device of claim 5, wherein the device comprises a configuration selected from the group consisting of a pin configuration, a hook-pin configuration, and a chip configuration.

9. The device of claim 5, wherein the at least one resorbable anchor portion comprises at least one barb and at least one point-tip.

10. The device of claim 5, wherein the at least one resorbable anchor portion comprises at least one coil.

11. The device of claim 5, wherein the tissue or organ within the mammalian body comprises a mammalian heart.

12. The device of claim 5, forming part of a system, the system further comprising:
a tube having a proximal end and a distal end, the tube defining a first opening at the proximal end and a second opening at the distal end, the tube sized and shaped to facilitate placement of the device within the mammalian body by delivering the device from the second opening of the tube to a location within the mammalian body.

13. The device of claim 12, wherein the system further comprises a shaft positioned within the tube, the shaft having a longitudinal axis, a proximal end, and a distal end, wherein the shaft is operable to facilitate placement of the device within the mammalian body.

14. The device of claim 13, wherein the system further comprises an embolus positioned at or near the distal end of the shaft, wherein the embolus is sized and shaped to facilitate placement of the device within the mammalian body.

15. The device of claim 13, wherein the shaft is rotatable about its longitudinal axis, and wherein the rotation of the shaft is operable to facilitate placement of the device within the mammalian body.

16. The device of claim 14, wherein the system further comprises a spring positioned at or near the distal end of the shaft between the shaft and the embolus, the spring capable to facilitate placement of the device for localized drug delivery within the mammalian body.

17. The device of claim 12, wherein the tube comprises an engagement catheter.

18. The device of claim 17, wherein the engagement catheter comprises a skirt positioned at the distal end of the engagement catheter, the skirt operable to reversibly engage a tissue or organ within the mammalian body to facilitate placement of the device within the mammalian body.

19. A device for localized drug delivery, the device comprising:
at least one drug release portion comprising a binder and at least one drug, the binder biologically degradable within a mammalian body at a first rate of degradation; and
at least one resorbable anchor portion forming the device with the at least one drug release portion and configured to fit within a pericardial space surrounding a heart and to actively engage and anchor to a surface of the heart, the at least one resorbable anchor portion biologically degradable within the mammalian body at a second rate of degradation that is slower than the first rate of degradation.

20. The device of claim 19, forming part of a system, the system further comprising:
a tube having a proximal end and a distal end, the tube defining a first opening at the proximal end and a second opening at the distal end, the tube sized and shaped to facilitate placement of the device within the pericardial space by delivering the device from the second opening of the tube to a location within the pericardial space; and
a shaft positioned within the tube, the shaft having a longitudinal axis, a proximal end, and a distal end, wherein the shaft is operable to facilitate placement of the device within the pericardial space.

* * * * *